(12) United States Patent
Bitter et al.

(10) Patent No.: US 10,159,661 B2
(45) Date of Patent: Dec. 25, 2018

(54) PENICILLIN RETARD COMPOSITION FOR INTRAMUSCULAR INJECTION

(71) Applicant: Sandoz AG, Basel (CH)

(72) Inventors: Christoph Bitter, Kundl (AT); Heiko Degendorfer, Kundl (AT); Johannes Raneburger, Kundl (AT)

(73) Assignee: Sandoz AG (CH)

( * ) Notice: Subject to any disclaimer, the term of this patent is extended or adjusted under 35 U.S.C. 154(b) by 0 days.

(21) Appl. No.: 15/552,067

(22) PCT Filed: Feb. 22, 2016

(86) PCT No.: PCT/EP2016/053625
§ 371 (c)(1),
(2) Date: Aug. 18, 2017

(87) PCT Pub. No.: WO2016/135075
PCT Pub. Date: Sep. 1, 2016

(65) Prior Publication Data
US 2018/0036291 A1 Feb. 8, 2018

(30) Foreign Application Priority Data

Feb. 23, 2015 (EP) ..................... 15156092

(51) Int. Cl.
| | | |
|---|---|---|
| *A61K 31/43* | (2006.01) | |
| *A61K 9/00* | (2006.01) | |
| *A61K 47/12* | (2006.01) | |
| *A61K 47/32* | (2006.01) | |
| *A61K 9/10* | (2006.01) | |
| *A61K 47/38* | (2006.01) | |
| *A61K 9/08* | (2006.01) | |
| *A61K 9/14* | (2006.01) | |
| *A61M 5/178* | (2006.01) | |

(52) U.S. Cl.
CPC ............ *A61K 31/43* (2013.01); *A61K 9/0019* (2013.01); *A61K 9/08* (2013.01); *A61K 9/10* (2013.01); *A61K 9/14* (2013.01); *A61K 47/12* (2013.01); *A61K 47/32* (2013.01); *A61K 47/38* (2013.01); *A61M 5/178* (2013.01)

(58) Field of Classification Search
CPC .. A61K 2300/00; A61K 31/43; A61K 31/495; A61K 31/431; A61K 31/496; A61K 47/12; A61K 47/26; A61K 9/0019
See application file for complete search history.

(56) References Cited

U.S. PATENT DOCUMENTS

| | | | | |
|---|---|---|---|---|
| 3,351,527 A | * | 11/1967 | Apat | ................... A61K 9/0019 424/497 |
| 4,518,606 A | | 5/1985 | Saias | |
| 6,207,661 B1 | * | 3/2001 | Thompson | ........... A61K 9/0019 514/192 |
| 2013/0189368 A1 | | 7/2013 | Mosqueira et al. | |

FOREIGN PATENT DOCUMENTS

GB 1151168 5/1969

OTHER PUBLICATIONS

International Search Report and Written Opinion for PCT/EP2016/053625, dated Jan. 9, 2016, 12 pages.

* cited by examiner

*Primary Examiner* — Audrea B Coniglio
(74) *Attorney, Agent, or Firm* — Luedeka Neely Group, P.C.

(57) ABSTRACT

The present invention is directed to an injection syringe comprising an injectable composition, the composition comprising a penicillin, salt or prodrug thereof, one or more pharmaceutically acceptable excipients, and water, wherein the composition is free of a preservative agent. In other aspects, the invention relates to a process for producing the injection syringe, and a kit comprising the injection syringe.

11 Claims, No Drawings

PENICILLIN RETARD COMPOSITION FOR INTRAMUSCULAR INJECTION

This application is a Section 371 national phase entry of PCT application PCT/EP2016/053625, filed Feb. 22, 2016. This application also claims the benefit of the earlier filing date of European patent application 15156092.7, filed Feb. 23, 2015.

The present invention is directed to an injection syringe comprising an injectable suspension, the composition comprising a penicillin, salt or prodrug thereof, one or more pharmaceutically acceptable excipients, and water, wherein the composition is free of a preservative agent. In other aspects, the invention relates to a process for producing the injection syringe, and a kit comprising the injection syringe.

BACKGROUND ART

Penicillin is a group of antibiotics, which were among the first drugs to be effective against many previously serious diseases, such as bacterial infections caused by staphylococci and streptococci. All penicillins are β-lactam antibiotics and are used in the treatment of bacterial infections caused by susceptible, usually Gram-positive, organisms.

Penicillins are widely used today for administration by injection, typically by use of ready-to-use syringes pre-filled with an injectable suspension containing the active agent. However, pre-filled injectable formulations containing penicillins generally contain preservatives in order to provide the required stability and sterility even after long term storage of the product.

The United States Pharmacopeia (USP) states in "Penicillin G Benzathine Injectable Suspension" that penicillin G benzathine injectable suspension is a sterile suspension of penicillin G benzathine in water for injection with one or more suitable buffers, dispersants, preservatives, and suspending agents. Hence, the USP recommends the presence of preservatives in penicillin injectable compositions.

Typical preservatives for pharmaceutical use are parabens or formaldehyde. In particular, parabens are used primarily for their bactericidal and fungicidal properties in many applications, such as pharmaceutical compositions.

However, the presence of preservatives in a medicament can lead to serious health problems and side effects, in particular when administered to children. Moreover, parabens contain methanol, ethanol and propanol as side product, which further increase the risk for side effects upon administration of the medicament. In addition, injectable compositions are generally sterilized by autoclaving. However, when parabens are used as preservatives autoclaving may lead to the formation of toxic compounds such as methanol and propanol in the product.

Parabens are further becoming increasingly controversial, however, because they have been found in breast cancer tumors. Parabens have also displayed the ability to slightly mimic estrogen, a hormone known to play a role in the development of breast cancer. Another concern is that the estrogen-mimicking aspect of parabens may be a factor in the increasing prevalence of early puberty in girls. Further, parabens can cause skin irritation and contact dermatitis and rosacea in individuals with paraben allergies.

A commercially available injectable formulation is for example Polyflex®, which is an ampicillin injectable suspension for veterinary use containing per vial 90 mg methylparaben and 10 mg propylparaben as preservative.

Bicillin® L-A is a penicillin G benzathine injectable formulation, provided as ready-to-use disposable syringe containing 0.1% methylparaben, and 0.01% propylparaben.

Cilicaine® is a procaine penicillin injectable formulation, containing phenyl mercuric acetate as preservative.

U.S. Pat. No. 3,351,527 is directed to stabilized benzathine penicillin compositions, which include a minor amount of sodium formaldehyde sulfoxylate as preservative component.

GB 1151168 is directed to a stabilized therapeutic composition for parenteral administration comprising benzathine penicillin G (N,N'-dibenzylethylenediamine dipenicillin) in an aqueous suspending medium which includes a wetting agent for the crystals, polyvinylpyrrolidone, and sodium formaldehyde sulphoxylate.

As penicillin's are generally provided in the form of an injectable suspension, the drug's release and resulting plasma concentration largely depend on the time needed for the active particles to solubilize in the patient's body. Therefore, it is difficult with the formulations of the prior art to provide a constant drug release and to maintain a uniform plasma concentration.

Therefore, a need exists in the art for the provision of a ready-to-use penicillin injectable formulation, which is stable on storage, and which overcomes the problems of the prior art. In particular, it is aimed to provide a ready-to-use injectable suspension, which maintains stability and sterility even in the absence of any preservative. Furthermore, it is aimed to provide a ready-to-use penicillin injectable retard formulation for providing a prolonged and constant release of the active agent into the patient's body and to maintain a uniform plasma concentration.

SUMMARY OF THE INVENTION

It has surprisingly been found in the present invention that the problems of the prior art can be solved by the provision of an injection syringe pre-filled with an injectable suspension comprising a penicillin, a salt or a prodrug thereof; one or more pharmaceutically acceptable excipients; and water, wherein the injectable suspension is free of a preservative agent.

Moreover, the present invention provides a process for the preparation of an injection syringe, the process comprising the steps of:
a) providing a solution of one or more pharmaceutically acceptable excipient in water, wherein the solution is free of a preservative agent,
b) sterilizing the solution of step a) to provide a sterile vehicle,
c) suspending sterile penicillin, its salt or prodrug in the vehicle, and
d) pre-filling the suspension in an injection syringe.

DETAILED DESCRIPTION OF PREFERRED EMBODIMENTS OF THE INVENTION

Injection Syringes

The present invention is directed to ready-to-use injection syringes, which are pre-filled with a pharmaceutical composition. The term "ready-to-use" in the context of the present invention typically means that no further preparation step is necessary before administering the pharmaceutical composition to the patient by injecting the composition. Moreover, there is no need to add further additives or solvents, such as water for injection, before administration of the pharmaceutical composition contained in the syringe. Synonymous terms used in the art are "pre-filled syringe" or "disposable syringe".

The ready-to-use injection syringes may be any typical syringe used for containing a pre-filled injectable composition, such as the commercially available syringe BD Hypak SC® syringe barrel with luer tip of 3 ml or 5 ml.

The injection syringe typically has a volume of from 0.5 ml to 10 ml, preferably from 1 ml to 6 ml, in particular may have a volume of 1 ml, 2 ml, 3 ml, 4 ml, 5 ml or 6 ml. In particular for paediatric purposes, also smaller injection volumes may be used, such as from 1 ml to 4 ml, preferably from 0.5 ml to 3 ml.

Further, the injection syringe pre-filled with the injectable suspension of the invention is sterile and thus can be stored until use without the necessity to apply any further sterilization steps. Sterility may be tested according to the US Pharmacopoeia (USP) 37 <1211> "Sterilization and Sterility Assurance of Compendial Articles", and the detailed description in USP Monograph: "Penicillin G Benzathine Injectable Suspension". Therefore, it is generally accepted that terminally sterilized injectable articles purporting to be sterile, when sterilized, attain a $10^{-6}$ microbial survivor probability, i.e., assurance of less than or equal to 1 chance in 1 million that viable microorganisms are present in the sterilized article or dosage form.

The injection syringe pre-filled with the injectable suspension of the invention is in particular intended for administration to a human subject.

Injectable Suspension

The injection syringe of the invention is pre-filled with a sterile injectable composition provided in the form of a suspension comprising, as pharmaceutically active agent, a penicillin. The term penicillin in the context of the present invention refers to any compound having antibiotic activity and comprising the core compound shown in the following formula:

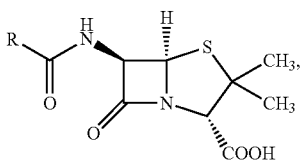

wherein "R" is a variable organic residue.

Typically, the term "penicillin" is used generically to refer to benzylpenicillin (penicillin G), procaine benzylpenicillin (penicillin procaine), benzathine benzylpenicillin (penicillin benzathine), and phenoxymethylpenicillin (penicillin V). Further, two or more penicillins can be used in combination. In a preferred embodiment the sterile injectable composition comprises a combination of penicillin G procain and penicillin G benzathine.

In a preferred embodiment, the penicillin is selected from penicillin procain, penicillin benzathine, and ampicilin. Preferably, the penicillin is penicillin G procain or penicillin G benzathine, most preferably is penicillin G benzathine. Penicillin G benzathine is represented by the following formula:

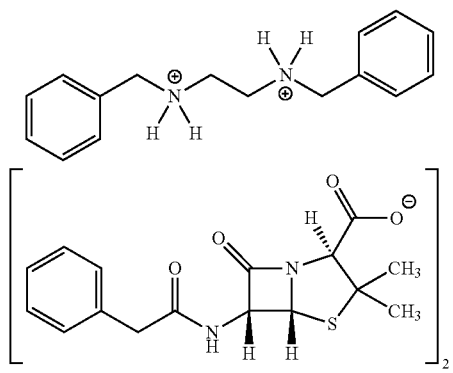

In a preferred embodiment, the pharmaceutically active agent consists of the penicillin, i.e. the penicillin is the only active agent contained in the injectable composition. In a particularly preferred embodiment, the active agent consists of penicillin G benzathine, i.e. penicillin G benzathine is the only active agent in the injectable composition.

The active agent is typically contained in the injectable suspension in a concentration between 5 and 80 wt. %, preferably between 10 and 60 wt. %, further preferably between 20 and 50 wt. %, most preferably about 40 wt. %. Further, the active agent is typically contained in the injectable suspension in an equivalent to 0.1 to 1.0 MIU/g, preferably 0.3 to 0.7 MIU/g, most preferably about 0.5 MIU/g.

The active agent further typically is provided in particular form. The particles of the active agent typically have an average particle diameter d(0.5), as measured by laser diffraction, in the range of from 1 μM to 100 μM, most preferably from 8 to 20 μM.

In the particle size distribution as measured by laser diffraction the value of d(0.1) is typically from 0.5 to 30 μM, preferably from 2.0 to 10 μM. The value of d(0.5) is typically from 1.0 to 100 μM, preferably from 8.0 to 20 μM. The value of d(0.9) is typically from 2.0 to 150 μM, preferably from 21 to 50 μM. The values of d(0.1/0.5/0.9) mean that 10 wt. %/50 wt. %/90 wt. % of the particles are smaller than the indicated particle size.

Laser diffraction may be measured by applying the following parameters:
Measurement range: 0.02-2000 μm
Optical model: Fraunhofer approximation
Mathematical model: General purpose, irregular shape
Measurement duration: 12 seconds
Sample dispersion time: 5 min in internal ultrasonic bath (30% level)
Stirring rate: 2000-2500 rpm
Obscuration: 10%

The composition contained in the injection syringe of the invention is in the form of a suspension. Typically, the active agent is suspended in the aqueous vehicle containing the one or more pharmaceutically acceptable excipients, while the pharmaceutically acceptable excipients are typically contained in the aqueous vehicle in the form of a solution.

The composition contained in the injection syringe of the invention is typically intended for intramuscular administration. It has been found in the invention that the intramuscular injection of the composition of the invention containing the active agent in particular form results in a prolonged/sustained release of the active agent. Accordingly, the injectable composition of the invention typically is a retard (depot) formulation, wherein the terms "retard", "depot formulation", "sustained release" and "prolonged release" can be used interchangeably.

In particular, injecting the active agent into the muscle in particular form has the effect that the active agent is slowly and uniformly released into the patient's body depending on the particle size. Thus, with the injectable compositions of the invention release of the active agent to the patient and duration of action of the active agent can be suitably controlled by adjusting the particle size of the active agent in the injectable suspension. In addition, uniformity of the patient's plasma concentration of the active agent can be increased.

In a particularly preferred embodiment, the composition contained in the injection syringe of the invention is suitable to provide release of the active agent to the patient's body within a period of 2 to 16 weeks, preferably within 4 to 12, most preferably within 6 to 10 weeks, although also shorter and longer durations may be possible depending on the particle size and amount of the active agent in the injectable composition.

It is possible with the injectable composition of the invention to prolong the drug's administration to once per week or even less frequently, such as once per two weeks or once per month. As a result, it is possible with the injectable composition of the invention to increase the patient's compliance.

The injectable composition may further contain one or more pharmaceutically acceptable excipients. The pharmaceutically acceptable excipient(s) is selected from buffers, tonicity adjusting agents, chelating agents, solubilising agents, thickeners, wetting agents, and antioxidants.

Buffers are added to a formulation to adjust and stabilize pH and optimize drug solubility and stability. The pH of the injectable composition is generally between pH 4 and 9, preferably between 5 and 7.5, most preferably is between 5.5 and 7.5, most preferably between 6.5 and 7.4. In a particularly preferred embodiment, the pH of the injectable composition has the pH of human blood, i.e. close to the physiologic pH between about 7.3 and 7.5.

Preferably, the buffer is selected from phosphate/phosphoric acid, citrate/citric acid, lactate/lactic acid, tartrate/tartaric acid and acetate/acetic acid. More preferably, the buffer is selected from phosphate/phosphoric acid, citrate/citric acid and acetate/acetic acid. Most preferred is citrate/citric acid.

Preferably, the buffer is present in the injectable composition at a concentration of 0.2 to 10 wt.-%, more preferably 0.4 to 6 wt.-%.

Tonicity adjusting agents are agents that control the tonicity of the injectable composition. Injectable compositions should be isotonic with human plasma so as to avoid damage to the tissues. Preferably, the tonicity agent is selected from dextrose, glycerol, sodium chloride, potassium chloride, mannitol or mixtures thereof. More preferably, the tonicity agent is selected from dextrose, glycerin, mannitol, sodium chloride or mixtures thereof. Most preferably, the tonicity agent is sodium chloride.

Preferably, the tonicity adjusting agent is present in the injectable composition at a concentration of 0.1 to 15 wt.-%, preferably 0.5 to 10 wt.-%.

A chelating agent can be defined as a substance whose molecules can form several bonds to a single metal ion. Preferably, the chelating agent is selected from one or more of calcium disodium ethylenediaminetetra acetic acid (EDTA), disodium EDTA, calcium versetamide sodium, calteridol, diethylenetriaminepenta acetic acid (DTPA).

Preferably, the chelating agent can be present in the injectable at a concentration in the range of 0.01 to 5 wt.-%.

Solubilising agents are agents which help in dissolving or increase the drug solubility into the formulation. The solubilising agents can be broadly classified into surfactants and co-solvents. The surfactants increase the dissolution by reducing the surface tension of the drug substances whereas co-solvents are defined as a solvent that in conjunction with another solvent can dissolve a solute. Preferably, the surfactant is selected from polyoxyethylene sorbitanmonooleate (Tween 80), sorbitan monooleate polyoxyethylenesorbitan monolaurate (Tween 20), lecithin, polyoxyethylene-polyoxypropylene copolymers (Pluronics) and mixtures thereof. Preferably, the co-solvent is selected from propylene glycol, glycerin, ethanol, polyethylene glycol (300 and 400), sorbitol, dimethylacetamide, cremophor EL and mixtures thereof. Further preferably, the solubilizing agent is Tween 80 or 20 or lecithin, most preferably is lecithin.

In a further preferred embodiment, the active agent is coated with the solubilizing agent. In a particular preferred embodiment, the active agent is coated with lecithin, and further preferably is coated with 0.5 to 2 wt. % lecithin, such as about 1 wt. % lecithin, on the basis of the amount of active agent.

Preferably, the solubilizing agent is present in the injectable composition at a concentration of 0.1 to 50 wt.-%, more preferably 0.4 to 10 wt.-%.

Thickeners are used to increase the viscosity of a solution or suspension and may also be referred to in the art as viscosity adjusting agents. Thickener(s) are typically selected from one or more of cellulose, cellulose ether or a salt thereof, polyvinylpyrrolidone (povidone), hyaluronic acid and gelatin. Preferably, the thickener is cellulose or cellulose ether.

A typical cellulose ether is selected from carboxymethyl cellulose, hydroxypropyl cellulose, hydroxypropyl methylcellulose, methylcellulose, ethyl cellulose, hydroxyethyl cellulose, optionally in their salt form, and mixtures thereof. More preferably the cellulose ether is selected from carboxymethyl cellulose, hydroxypropyl methylcellulose, methyl cellulose, optionally in their salt form, and mixtures thereof. Most preferably, the cellulose ether is carboxymethyl cellulose (CMC).

Preferably, the injectable suspension contains the thickener in a concentration in the range of 0.02 to 20% by weight, preferably 0.05 to 10%, more preferably 0.08 to 5%, most preferably 0.1 to 2%.

Wetting agents reduce the contact angle between the surface of the particle and the wetting liquid to obtain maximum wetting efficiency. Typical wetting agents are non-ionic surfactants and non-aqueous solvents. Preferably, surfactants with a hydrophilic lipophilic balance (HLB) value in the range of 7 to 9 are selected. Preferably, the wetting agent is selected from glycerin, propylene glycol, lecithin, polysorbate 20, polysorbate 80, pluronic F-68, sorbitantrioleate (span 85) and mixtures thereof.

Preferably, the concentration of wetting agent in the injectable composition is in the range of 0.02 to 1.0 wt.-%.

Antioxidants are used to prevent/minimize the oxidation reaction of the API or excipients over the shelf life of the product whereas antimicrobial agents are used to prevent the growth of micro-organisms in the API product. Typical antioxidants are selected from ascorbic acid, acetylcysteine, sulfurous acid salts (bisulfite, metabisulfite), monothioglycerol, citric acid or mixtures thereof.

Preferably, the concentration of antioxidant in the injectable composition is in the range of 0.01 to 5.0 wt.-%.

The injectable composition is substantially free from preservatives, which are also referred to in the art as antimicrobial agent. Substantially free means that the amount of preservatives or antimicrobial agents in the injectable composition is below 0.01 wt.-%, preferably below 0.001 wt-%. In the most preferred embodiment, the injectable composition is free of preservatives.

Typical preservatives or antimicrobial agents, which are contained in the compositions of the prior art, are selected from e.g. formaldehyde, phenol, meta-cresol, benzyl alcohol, parabens (for example methyl, propyl, butyl), benzalkonium chloride, chlorobutanol, thimerosal, phenylmercuric salts (acetate, borate, nitrate) or mixtures thereof. Propyl, methyl and butyl parabens are referred to chemically as propyl methyl and butyl esters of p-hydroxy benzoic acid. In a preferred aspect, the injectable composition is free from parabens.

Process for the Preparation of an Injection Syringe

In a further embodiment, the invention is directed to a process for the preparation of an injection syringe pre-filled with an injectable composition as described above.

Hence, in a preferred embodiment, the invention is directed to a process for the preparation of an injection syringe pre-filled with an injectable composition, the process comprising the steps of
a) providing a solution of the one or more pharmaceutically acceptable excipient in water, wherein the solution is free of a preservative agent,
b) sterilizing the solution of step a) to provide a sterile vehicle,
c) suspending sterile penicillin, its salt or prodrug in the vehicle, and
d) pre-filling the suspension in an injection syringe.

In a particularly preferred embodiment, sterilizing in step b) is performed by steam sterilization (autoclaving) or sterile filtration, preferably by steam sterilization. Typical conditions for obtaining the desired sterility are described for example in the US Pharmacopoeia (USP) 37<1211>, "Sterilization and Sterility Assurance of Compendial Articles".

The process of thermal sterilization employing saturated steam under pressure ("steam sterilization") is typically carried out in a chamber called an autoclave. The basic principle of operation is that the air in the sterilizing chamber is displaced by the saturated steam, achieved by employing vents or traps. In order to displace air more effectively from the chamber and from within articles, the sterilization cycle may include air and steam evacuation stages. Sterilization is generally performed at 121° C. for at least 20 min. Sterilization cycle parameters, when using a temperature other than 121°, in the F0 concept may be appropriate. The F0, at a particular temperature other than 121°, is the time (in minutes) required to provide the lethality equivalent to that provided at 121° for a stated time. Other combinations of temperature and time may also be used and are known to the skilled person for obtaining the desired level of sterility of the final product.

Filtration for sterilization purposes is usually carried out with assemblies having membranes of nominal pore size rating of 0.22 µm or less, preferably 0.20 µm or less, more preferably 0.10 µm or less. Preferably, the sterile filter is made of polyethersulfone (PES), cellulose nitrate, polyvinylidene fluoride (PVDF) or mixtures thereof. Preferably, the sterile filter is made of polyethersulfone.

Kits

Also provided are kits comprising one or more of the pre-filled injection syringe of the invention. In one embodiment, such a kit comprises one or more pre-filled syringe of the invention in a blister pack. The blister pack may itself be sterile on the inside. In one embodiment, injection syringes according to the invention may be placed inside such blister packs prior to undergoing sterilisation, for example terminal sterilisation.

Such a kit may further comprise a needle for administration of the injectable composition. It is typical to use a 18-gauge (1.27 mm) needle, though 29-gauge (0.358 mm), 21-gauge (0.873 mm) or other needle diameters may also be used, e.g. depending on the particle size of the active agent in the injectable suspension.

The present invention thus provides for an injection syringe for the intramuscular administration of a penicillin, which avoids the use of any preservative, thereby preventing side effects or any health problems resulting from the preservative, such as parabens. Moreover, the present invention avoids side effects resulting from toxic compounds, which might stem from sterilization of the preservative in the injectable composition. For example, the present invention prevents any toxic agents resulting from degradation of parabens, such as methanol, and the side effects resulting from such compounds.

As a result of the avoidance of any preservatives, the injectable composition contained in the injection syringes of the invention is more suitable for children. Further, as side effects can be reduced, the product of the invention provides added value for the patient.

In addition, the injection syringe of the invention allows for easier production of the product, as no heating step to solubilize the preservative such as parabens is necessary.

Further, it could be surprisingly shown that the product as described herein is sufficiently stable even after long term storage and remains sterile even in the absence of any preservative.

The invention is further described by the following non-limiting examples.

EXAMPLES

Example 1: Preparation of an Injectable Composition

An injectable composition has been prepared by dissolving all excipients of the vehicle in water for injection, autoclaving the vehicle at 121° C. for 20 min, suspending sterile penicillin G benzathine in the autoclaved vehicle, and filling the suspension in syringes ready for use.

The composition of the vehicle was as follows:

| | |
|---|---|
| Sodium carboxymethyl cellulose (CMC) Type 7HF | 0.58 g |
| Povidon K30 | 0.58 g |
| Citric acid | 0.025 g |
| Trisodium citrate | 0.867 g |
| Water for injection | ad 59.753 g |
| Suspending of API: | |
| API: penicillin G benzathine | 40.247 g |

Example 2: Preparation of an Injectable Composition

An injectable composition has been prepared by dissolving all excipients of the vehicle in water for injection, autoclaving the vehicle at 121° C. for 20 min, suspending sterile penicillin G benzathine in the autoclaved vehicle, and filling the suspension in syringes ready for use.

The composition of the vehicle was as follows:

| | |
|---|---|
| Sodium carboxymethyl cellulose (CMC) Type 7HF | 0.547 g |
| Povidon K30 | 0.547 g |
| Citric acid | 0.049 g |
| Trisodium citrate | 0.961 g |
| Water for injection | ad 59.989 g |
| Suspending of API: | |
| API: penicillin G benzathine | 40.011 g |

Example 3: Determination of Methanol Content

The content of methanol was determined for compositions of Examples 1 and 2 and compared to a commercial composition (penicillin G benzathine injectable suspension marketed in US, containing 0.1% methylparaben, and 0.01% propylparaben) by gas chromatography (GC) measurement. The results are shown in the following Table.

| | Amount of Methanol | | |
|---|---|---|---|
| Composition | (µg/mg) | Wt. % | µg/syringe |
| Example 1 | 0.006 | 0.0006 | 30 (2.4 MIU syringe) |
| Example 2 | 0.003 | 0.0003 | 4 (0.6 MIU syringe) |
| Comparative Example | 0.089 | 0.0089 | 461 (2.4 MIU syringe) |

Example 4: Determination of Storage Stability

Stability of the injectable suspension of Example 2 has been determined after 1 and 3 months of storage at different storage conditions. The results are shown in the Tables below.

a) Stability Data of Example 2 at 25°/65% r.H.

| parameter | Initial | 1 month | 3 months |
|---|---|---|---|
| appearance of suspension | viscous white suspension | viscous white suspension | viscous white suspension |
| ph value | 6.1 | 6.1 | 6.1 |
| density [g/mL] | 1.08 | 1.08 | 1.08 |
| impurities [sum in %] | 0.9 | 0.9 | 1.1 |
| assay of Penicillin G Benzatine [% of Declaration (2.4 MIU syringe)] | 104 | 106 | 105 | b) Stability Data of Example 2 at 5° C.

| parameter | Initial | 3 months |
|---|---|---|
| appearance of suspension | viscous white suspension | viscous white suspension |
| ph value | 6.1 | 6.1 |
| density [g/mL] | 1.08 | 1.08 |
| impurities [sum in %] | 0.9 | 1.1 |
| assay of Penicillin G Benzatine [% of Declaration (2.4 MIU syringe)] | 104 | 106 |

It could be shown by the above comparison of the injectable suspensions of the invention with a commercially available injectable suspension of the prior art that the injectable suspensions of the present invention, which do not contain any preservatives, such as parabens, have significantly reduced methanol content compared to the paraben containing injectable suspension of the prior art, but maintain long term stability and sterility. Thus, the health problems which can result from the use of preservative agents such as parabens in injectable suspensions of the prior art can be avoided without affecting product stability.

The invention claimed is:

1. Disposable injection syringe pre-filled with an injectable suspension, the suspension comprising:
   a) a pharmaceutical active agent selected from one or more of benzylpenicillin, penicillin G procain, penicillin G benzathine, ampicillin, and phenoxymethyl penicillin, a salt or a prodrug thereof,
   b) one or more pharmaceutically acceptable excipient, and
   c) water,
wherein the suspension is free of a preservative agent selected from formaldehyde, phenol, meta-cresol, benzyl alcohol, parabens, benzalkonium chloride, chlorobutanol, thimerosal, phenylmercuric salts or mixtures thereof.

2. Disposable injection syringe of claim 1, wherein the penicillin is a combination of penicillin G procain and penicillin G benzathine.

3. Disposable injection syringe of claim 1, wherein the pharmaceutically acceptable excipient is selected from buffers, tonicity adjusting agents, chelating agents, solubilising agents, thickeners, and wetting agents.

4. Disposable injection syringe of claim 3, wherein the buffer is selected from phosphate/phosphoric acid, citrate/citric acid, lactate/lactic acid, tartrate/tartaric acid and acetate/acetic acid.

5. Disposable injection syringe of claim 3, wherein the thickener is selected from cellulose, cellulose ether, optionally in its salt form, polyvinylpyrrolidone, hyaluronic acid, gelatin, or combinations thereof.

6. Disposable injection syringe of claim 1, wherein the pharmaceutically active agent has an average particle diameter as determined by laser diffraction from 1 to 100 µm.

7. Disposable injection syringe of claim 1, wherein the penicillin, its salt or prodrug is coated with a solubilising agent.

8. Process for the preparation of a disposable injection syringe according to claim 1, the process comprising the steps of:
   a) providing a solution of the one or more pharmaceutically acceptable excipient in water, wherein the solution is free of a preservative agent,
   b) sterilizing the solution or suspension of step a) to provide a sterile vehicle,
   c) suspending sterile penicillin, its salt or prodrug in the vehicle, and
   d) pre-filling the suspension in an injection syringe
wherein the penicillin is selected from one or more of benzylpenicillin, penicillin G procain, penicillin G benzathine, ampicillin, and phenoxymethyl penicillin, and
wherein the preservative agent is selected from formaldehyde, phenol, meta-cresol, benzyl alcohol, parabens, benzalkonium chloride, chlorobutanol, thimerosal, phenylmercuric salts or mixtures thereof.

9. Process of claim 8, wherein sterilizing in step b) is performed by steam sterilization.

10. Kit comprising one or more of the disposable injection syringe according to claim 1, and optionally one or more needles.

11. Disposable injection syringe according to claim 1 for use in the administration of an injectable suspension to a human subject, the injectable suspension comprising:
- a) a pharmaceutical active agent selected from one or more of benzylpenicillin, penicillin G procain, penicillin G benzathine, ampicillin, and phenoxymethyl penicillin, a salt or a prodrug thereof,
- b) one or more pharmaceutically acceptable excipient, and
- c) water, wherein the suspension is free of a preservative agent selected from formaldehyde, phenol, meta-cresol, benzyl alcohol, parabens, benzalkonium chloride, chlorobutanol, thimerosal, phenylmercuric salts or mixtures thereof.

* * * * *